(12) United States Patent
Sheehan et al.

(10) Patent No.: US 11,529,269 B2
(45) Date of Patent: Dec. 20, 2022

(54) ABSORBENT ARTICLE PACKAGE WITH ENHANCED OPENING AND RECLOSEABILITY

(71) Applicant: The Procter & Gamble Company, Cincinnati, OH (US)

(72) Inventors: Astrid Annette Sheehan, Cincinnati, OH (US); Oliver Edwin Clarke Mason, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/739,223

(22) Filed: May 9, 2022

(65) Prior Publication Data
US 2022/0304868 A1 Sep. 29, 2022

Related U.S. Application Data

(63) Continuation of application No. 16/686,651, filed on Nov. 18, 2019, now Pat. No. 11,364,160.

(30) Foreign Application Priority Data

Nov. 22, 2018 (EP) ..................... 18207836

(51) Int. Cl.
*B65D 73/00* (2006.01)
*A61F 13/551* (2006.01)
*A61F 13/15* (2006.01)

(52) U.S. Cl.
CPC .... *A61F 13/5514* (2013.01); *A61F 13/15747* (2013.01); *A61F 2013/55195* (2013.01)

(58) Field of Classification Search
CPC ............... B65D 75/58; B65D 75/5811; B65D 75/5827; B65D 85/07; A61F 13/5514; A61F 13/15747; A61F 2013/55195
(Continued)

(56) References Cited

U.S. PATENT DOCUMENTS 3,929,678 A 12/1975 Laughlin et al.
4,259,217 A 3/1981 Murphy
(Continued)

FOREIGN PATENT DOCUMENTS

CN 103635400 A 3/2014
CN 203854962 U 10/2014
(Continued)

OTHER PUBLICATIONS

All Office Actions; U.S. Appl. No. 16/686,651, filed Nov. 18, 2019.
(Continued)

*Primary Examiner* — Luan K Bui
(74) *Attorney, Agent, or Firm* — Amanda Herman Berghauer

(57) ABSTRACT

A package containing a stack of folded disposable absorbent articles, the package being formed of flexible polymeric film, and having a path of perforations or scoring defining a hood opening structure, is disclosed. The hood opening structure may be configured to open proximate the fold noses of the articles for easy tactile identification, grasping and withdrawal of individual ones thereof, and may be configured so as to serve as an effective package reclosure device whereby the package may be used to store the unused supply of articles following opening. The package, and printed commercial artwork and product information on the package surfaces, may be configured such that the fold noses are disposed at the apparent bottom of the package, for improved standing stability when the package is shelved.

20 Claims, 16 Drawing Sheets

(58) Field of Classification Search
USPC .......................... 206/440, 441, 491; 229/240
See application file for complete search history.

(56) References Cited

U.S. PATENT DOCUMENTS

| | | | |
|---|---|---|---|
| 5,048,687 | A | 9/1991 | Suzuki et al. |
| 5,150,561 | A | 9/1992 | Muckenfuhs |
| 5,261,899 | A | 11/1993 | Visscher |
| 5,380,094 | A | 1/1995 | Schmidt |
| 5,655,843 | A | 8/1997 | Conrad et al. |
| 5,967,665 | A | 10/1999 | Macdonald et al. |
| 6,258,308 | B1 | 7/2001 | Brady |
| 8,074,803 | B2 * | 12/2011 | Motsch .............. B65D 75/5833 383/207 |
| 8,114,522 | B2 | 2/2012 | Kitora |
| 8,490,793 | B2 * | 7/2013 | Evenson ............ B65D 75/5833 383/207 |
| 9,169,366 | B2 | 10/2015 | Weisman et al. |
| 2002/0112982 | A1 | 8/2002 | Stagray et al. |
| 2006/0021894 | A1 | 2/2006 | Clark, Jr. et al. |
| 2006/0131200 | A1 | 6/2006 | Boldra et al. |
| 2009/0255847 | A1 | 10/2009 | Motsch et al. |
| 2010/0159167 | A1 | 6/2010 | Schumacher |
| 2011/0132783 | A1 * | 6/2011 | Williams ............ B42D 25/465 235/487 |
| 2012/0023774 | A1 | 2/2012 | Garcia |
| 2015/0010462 | A1 | 1/2015 | Kawauchi |
| 2015/0026666 | A1 | 1/2015 | Tojo |
| 2015/0343374 | A1 | 12/2015 | Augustsson |
| 2018/0036584 | A1 | 2/2018 | Kleman |
| 2018/0118436 | A1 | 5/2018 | Sheehan |
| 2018/0289564 | A1 | 10/2018 | Sheehan |
| 2020/0163813 | A1 | 5/2020 | Sheehan et al. |

FOREIGN PATENT DOCUMENTS

| | | |
|---|---|---|
| CN | 205668700 U | 11/2016 |
| DE | 4224639 A1 | 1/1994 |
| EP | 0414549 | 12/1994 |
| WO | 9308874 A1 | 5/1993 |
| WO | 9308876_ | 5/1993 |
| WO | 9920664 A3 | 11/1999 |
| WO | 2006017518 A2 | 2/2006 |
| WO | 2006047374 A1 | 5/2006 |
| WO | 2008086539 A3 | 12/2008 |

OTHER PUBLICATIONS

EP Search Report and Written Opinion for 18207836.0 dated May 22, 2019, 4 pages.
Extended European Search Report and Search Opinion; Application No. PCT/US2019/062719; dated Feb. 28, 2020; 10 pages.

* cited by examiner

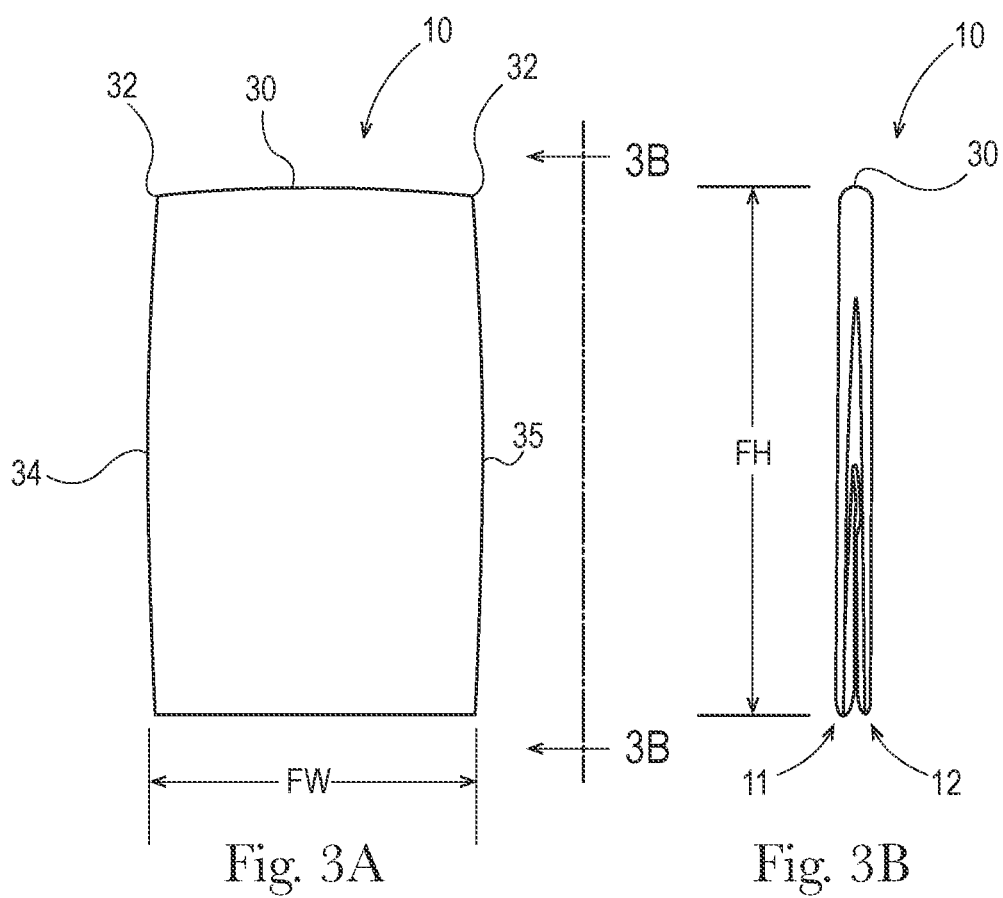

ABSORBENT ARTICLE PACKAGE WITH ENHANCED OPENING AND RECLOSEABILITY

CROSS REFERENCE TO RELATD APPLICATION

This application is a continuation of U.S. patent application Ser. No. 16/686,651, filed on Nov. 18, 2019, which claims priority to European Patent Application No. 18207836.0, filed Nov. 22, 2018, the entire disclosures of both of which are incorporated herein by reference.

FIELD OF THE INVENTION

The present invention relates to a film package for disposable absorbent articles, comprising opening features designed to open easily but not unintentionally.

BACKGROUND OF THE INVENTION

Non-fragile, compressible consumer products such as disposable absorbent articles (e.g., diapers and training pants, disposable adult incontinence pants and feminine hygiene pads) are often packaged and sold at retail (i.e., placed on display and for sale in a retail store) in soft packages formed of polymer film. Such packages may be formed from one or more sheets of polymer film, seamed via application of heating energy, which has caused portions of the film to melt and fuse along the seams.

After opening a package of disposable absorbent articles and removing one or more items needed for immediate use, a consumer may wish to leave the remaining unused supply of product in the package for storage until the next time additional items are needed. Thus, it is often desirable that the package retain, to some extent, its shape and structural integrity to remain useful as a container for storing unused product following opening. Additionally, and particularly in environments where high humidity and substantial quantities of airborne dust and dirt particles may be present, it may be desired that the package not only retain its shape and structural integrity, but have a recloseability capability that allows the package to be reclosed to an extent suitable to help protect the unused product from airborne contaminants.

To date, film package opening features have generally been less than fully satisfactory. Various prior configurations of opening perforations have not provided easy opening features, and in addition or alternatively, tend to promote substantial destruction of the package during opening, rendering it unsatisfactory for use as a storage container. US 2018/0118436 by the Procter & Gamble Company tackles the problem to some extent, by providing continuous perforations along a path extending across three surfaces of a package, 40 mm from the top surface. This provides an easy opening mechanism for consumers and creates a reclosable "hood" after opening, thus enabling consumers to close the pack after use. However, such a package has limitations when the contents are heavy and/or when the packaging film is thin.

Consequently, there is room for improvement in film package opening features.

SUMMARY OF EXEMPLARY FORMS

The present invention is directed to package formed of flexible polymeric film, enclosing and wrapping a stack of folded disposable absorbent articles having an approximate rectangular cuboid shape, the package comprising front, rear, first and second side walls and a top and bottom surface, defining an approximate rectangular cuboid shape, at least one seam extending from the top to the bottom surface of one of said side walls, a first perforation line extending from said seam partway along the front wall, a second perforation line extending from said seam partway along the rear wall, a stress dispersion area between the first perforation line and said second perforation line, wherein said stress dispersion area extends over said seam and is at least 8 mm long.

The present inventors have found that while perforations are useful for enabling easy and clean opening of such flexible polymeric films, in some circumstances, e.g., for heavy packages and/or for thin or weak films, the perforation may be prone to early and unintentional opening—particularly in areas where stress may be applied in a concentrated manner. For example, the area of the seam leads to a gusset formed at the top and bottom of at least one of the side walls. Buyers often grab the bag in the area of the gusset upon purchase thus introducing stress along the short wall, at the top of the seam. In such circumstances, without the stress dispersion area, the bag may prematurely open. This is also the case for other handles that are in line with the seam. Thus, in the present invention, a stress dispersion area is provided that extends over the seam. The length of the stress dispersion area addresses the need for balance between avoiding unintentional and premature opening of the package, while still enabling easy and neat opening.

BRIEF DESCRIPTION OF THE FIGURES

FIG. 3A is a plan view of the diaper of FIG. 2, shown folded about a lateral fold line, wearer-facing surfaces in and outward-facing surfaces out.

FIG. 3B is an edge side view of the folded diaper shown in FIG. 3A.

DESCRIPTION OF EXAMPLES

Definitions

Figure 1:
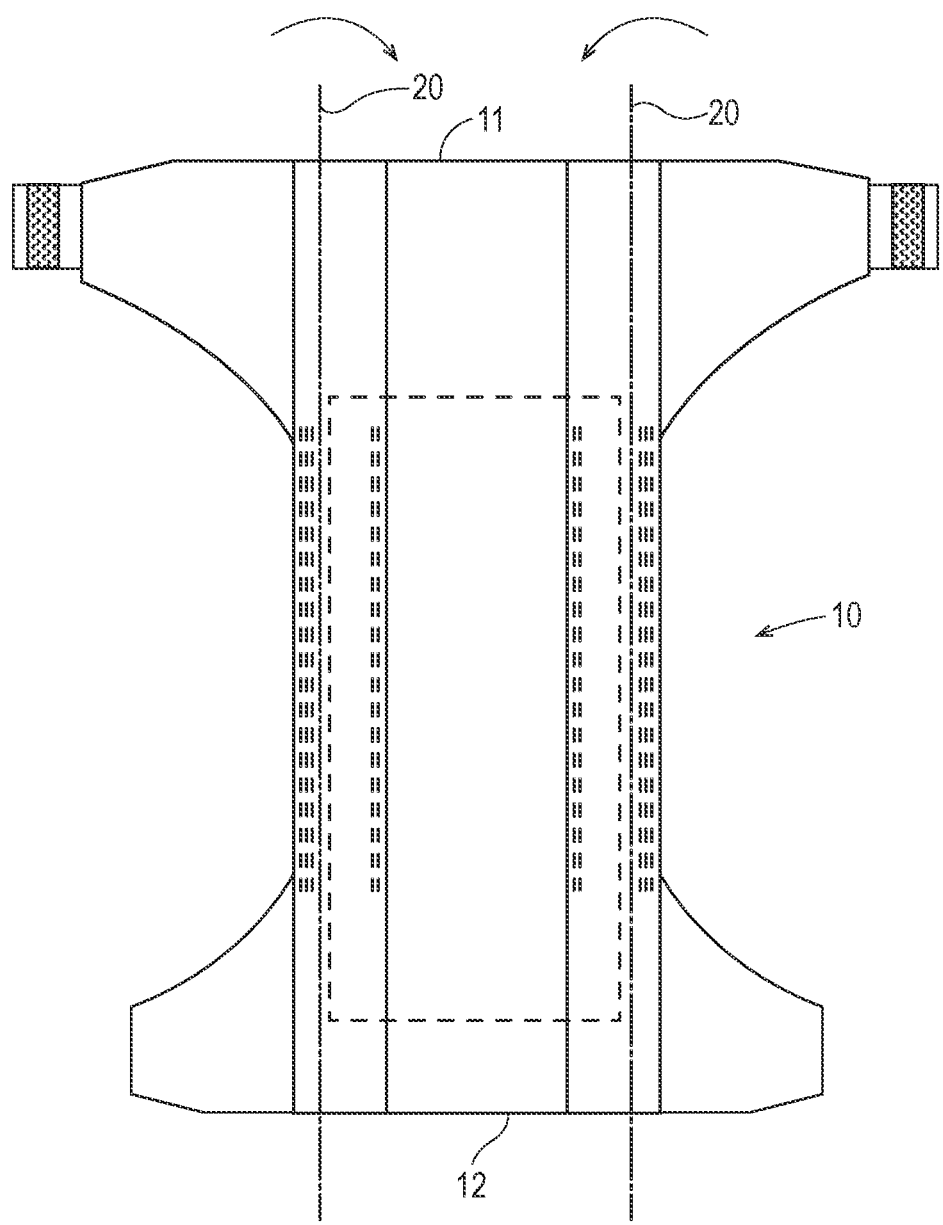
FIG. 1 is a plan view of an example of a disposable absorbent article in the form of a disposable diaper, wearer-facing surfaces facing the viewer.

"Film" means a sheet structure having a length, width and thickness (caliper), wherein each of the length and width greatly exceed the thickness, i.e., by a factor of 1,000 or more, the structure having one layer (monolayer) or more respectively adjacent layers (multilayer), each layer being a substantially continuous structure formed of one or more thermoplastic polymer resins (including blends thereof).

"High Density Polyethylene" (HDPE) means a type of polyethylene defined by a density equal to or greater than 0.941 g/cm$^3$.

"Low Density Polyethylene" (LDPE) means a type of polyethylene defined by a density equal to or less than 0.925 g/cm$^3$.

"Medium Density Polyethylene" (MDPE) means a type of polyethylene defined by a density range of 0.926-0.940 g/cm$^3$.

With respect to a disposable diaper, disposable absorbent pant, or feminine hygiene pad, "lateral" and forms thereof refer to a direction parallel with the waist edges and/or perpendicular to the direction of wearer's standing height when the article is worn.

"Linear Low Density Polyethylene" (LLDPE) means a type of Low Density Polyethylene characterized by substantially linear polyethylene, with significant numbers of short branches, commonly made by copolymerization of ethylene with longer-chain olefins. Linear low-density polyethylene differs structurally from conventional low-density polyethylene (LDPE) because of the absence of long chain branching. The linearity of LLDPE results from the different manufacturing processes of LLDPE and LDPE. In general, LLDPE is produced at lower temperatures and pressures by copolymerization of ethylene and such higher alpha-olefins as butene, hexene, or octene. The copolymerization process produces a LLDPE polymer that has a narrower molecular weight distribution than conventional LDPE and in combination with the linear structure, significantly different rheological properties.

With respect to a disposable diaper, disposable absorbent pant, or feminine hygiene pad, "longitudinal" and forms thereof refer to a direction perpendicular with the waist edges and/or parallel to the direction of the wearer's standing height when the article is worn.

With respect to quantifying the weight fraction or weight percentage of a component of a polymer resin composition forming a film or layer thereof, "predominately" (or a form thereof) means that the component constitutes the largest weight fraction or weight percentage among all components of the composition.

Package; Packaging Film

Referring to FIGS. 1 through 5C, a retail package 49 of non-fragile, compressible disposable absorbent articles 10 (such as, for example, disposable diapers, training pants or adult incontinence pants) may be formed of a polymer film. The film may be a single layer (monolayer), or may have two, three or more layers (multilayer). A multilayer film may have, for example, an outer skin layer formed of a first polymer and an inner skin layer formed of a second polymer. (As used herein, the terms "outer" and "inner" refer to the positioning of the layer relative the inside and the outside of the finished package; thus, the "inner layer" faces the contained product, and the "outer layer" faces outward and has an outer surface that is exposed to view and touch by, e.g., shoppers in a retail store.)

Figure 2:
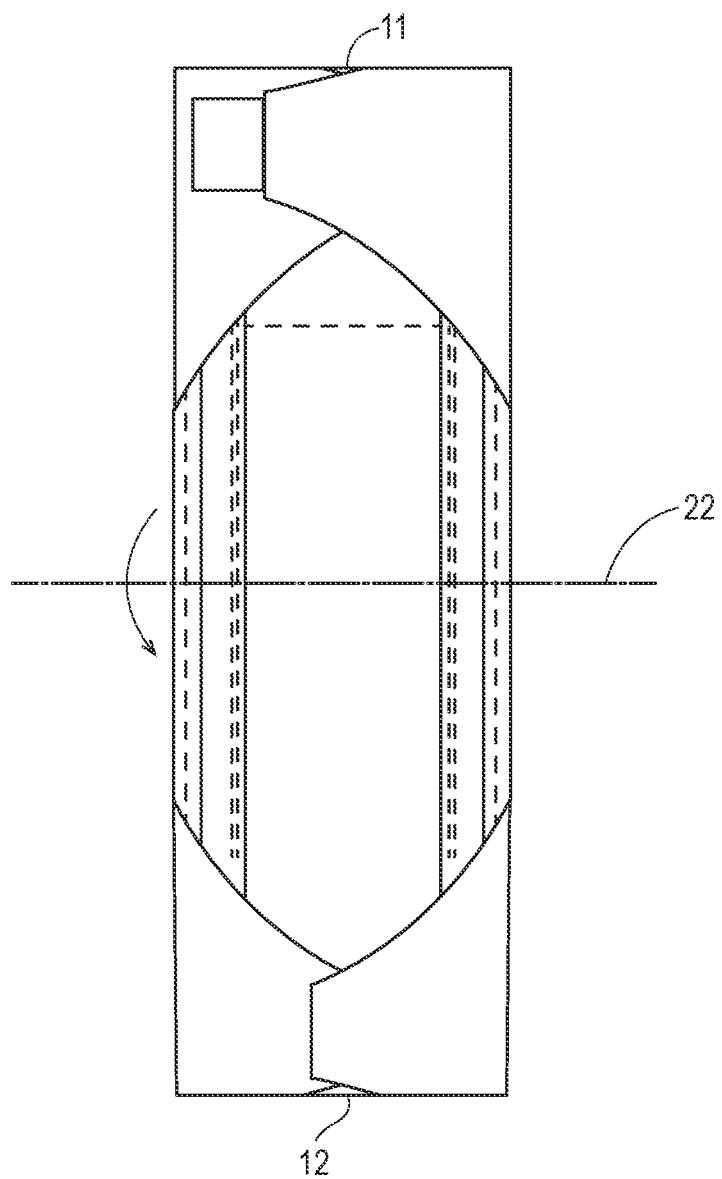
FIG. 2 is a plan view of the diaper of FIG. 1, shown with side portions folded over and laterally inward about longitudinal side edge fold lines.
Figure 4A:
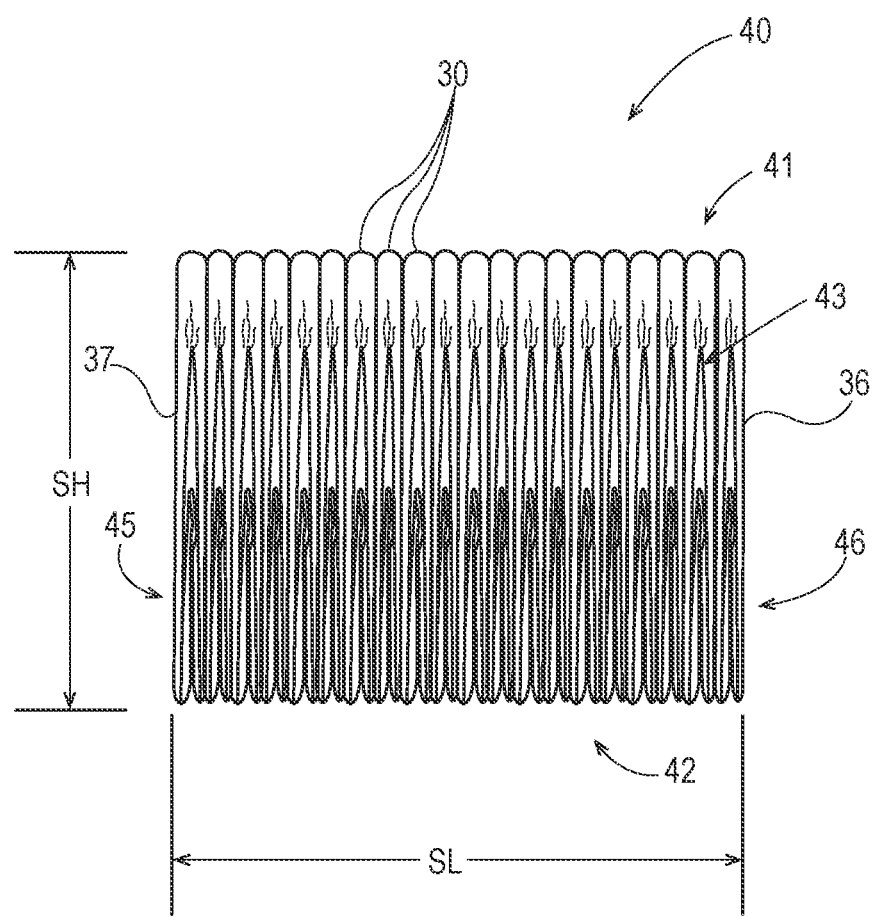
FIG. 4A is an edge side view of a stack of a plurality of folded diapers such as the folded diaper shown in FIGS. 3A and 3B.
Figure 4B:
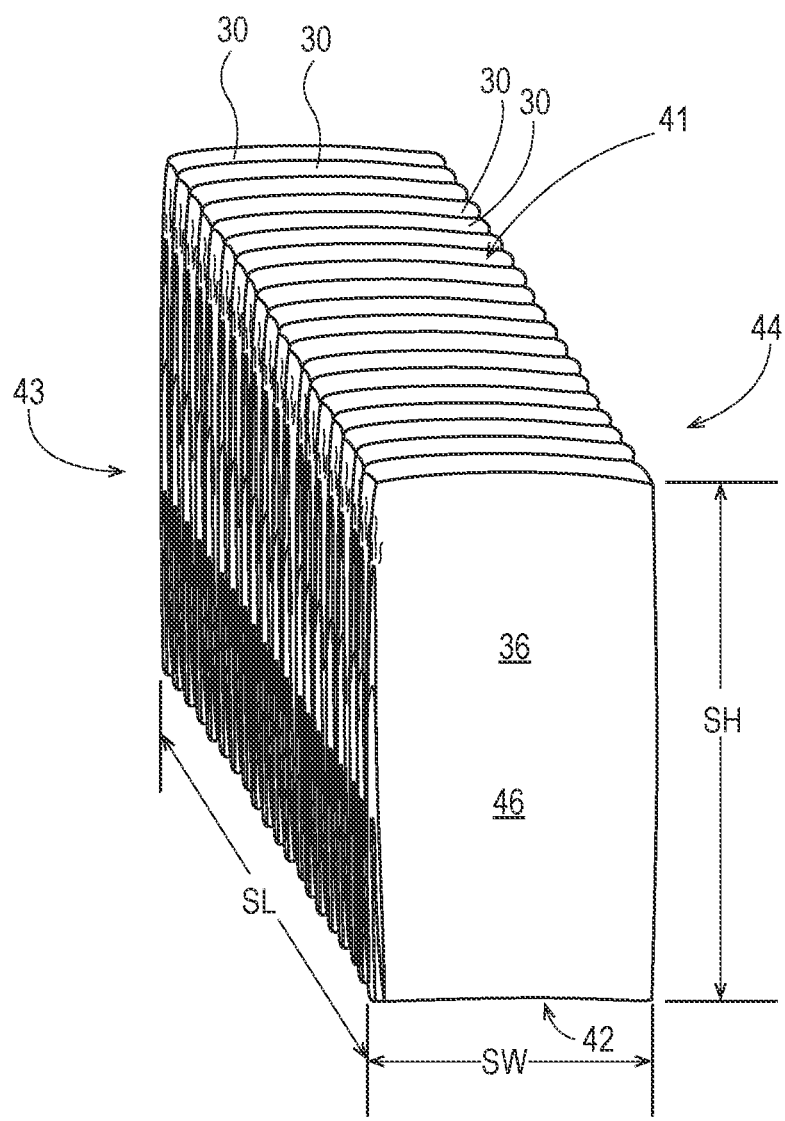
FIG. 4B is a perspective view of the stack of FIG. 4A.

FIGS. 1-3 depict an example of a disposable diaper with front and rear waist edges 11, 12, in successively open/unfolded and folded. FIGS. 4A and 4B depict a stack of a plurality of disposable diapers such that depicted in FIGS. 1-3. For packaging in bulk, each of a plurality of disposable diapers such as that shown in FIG. 1 may, in a possible first step, have its longitudinal side portions be folded over and laterally inward about longitudinal side edge fold lines 20, as may be appreciated from a comparison of FIGS. 1 and 2. Next, the diaper may, in a second step, be folded longitudinally, about lateral fold line 22 that passes through the crotch region of the diaper, as may be appreciated from a comparison of FIGS. 2 and 3. For a bi-fold configuration such as depicted in FIGS. 3A, 3B and 4, the article may be folded longitudinally once, and may in some examples be folded approximately in half about the lateral fold line. For a tri-fold configuration (not shown), the article may be folded longitudinally twice, about two longitudinally-spaced lateral fold lines. In some examples a tri-fold configuration may have the article folded approximately in thirds, about the two longitudinally-spaced lateral fold lines.

Regardless of whether the article is in a bi-fold or tri-fold configuration, the folded article such as folded diaper 10 will have a single fold nose 30 defining at least one end edge of the folded article, fold nose corners 32, and left and right side edges 34, 35. (It will be appreciated that in a tri-fold example, a single fold nose may define each of both end edges of the folded article.) In some examples such as depicted in FIGS. 3A and 3B, fold nose 30 may be proximate the crotch region of the article (the middle region of the article adapted to be located between the wearer's legs during wear). The folded article will have a folded width FW measured as the distance between side edges, and a folded height FH measured as the distance between end edges. A plurality of folded articles such as depicted in FIGS. 3A and 3B may then be placed in similar orientation and neatly stacked together face-to-face to form a stack 40 such as depicted in FIGS. 4A and 4B. In another example (not shown), a first set of the plurality of folded articles may have their fold noses oriented along one side of the stack, and a second set of the plurality of folded articles may be rotated 180 degrees to have their fold noses oriented along the opposite side of the stack. In some examples, the articles in the first set and the articles in the second set may appear in alternating sequence in the stack. For purposes of economy of space in packaging, packing, shipping and shelving, stack 40 may be compressed to a desired degree of compression, along the stack direction SD.

Referring to FIGS. 4A and 4B, stack 40 will have an approximate rectangular cuboid form with a stack height SH approximately corresponding to the folded height FH of the individual folded articles, a stack width SW approximately corresponding to the folded width FW of the individual folded articles, and a stack length SL measured from a first outward-facing side 36 of a first article in the stack to an opposing second outward-facing side 37 of a last article in the stack, along stacking direction SD. Stack 40 may have a first side 41 and an opposing second side 42, one or both of which are defined by approximately aligned fold noses of folded articles in the stack. Stack 40 may have opposing third and fourth sides 43, 44, both of which are defined by approximately aligned side edges 34, 35 of folded articles in the stack. Stack 40 may have opposing fifth and sixth sides 45, 46, each of which is defined by one of first and second outward facing sides 36, 37 of first and last articles at each end of the stack.

Figure 5A:
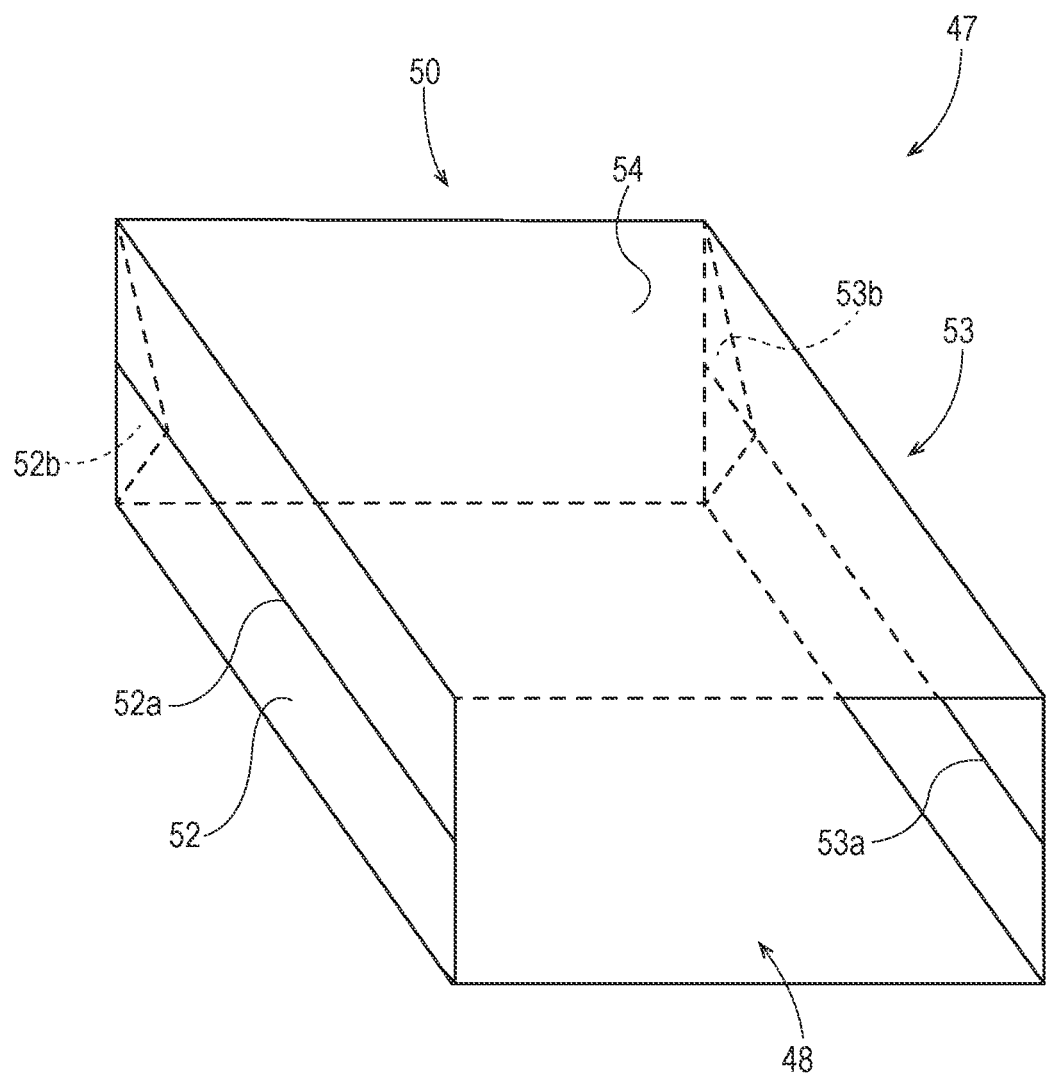
FIG. 5A is a perspective view of a film bag structure from which a film package may be formed.
Figure 5B:
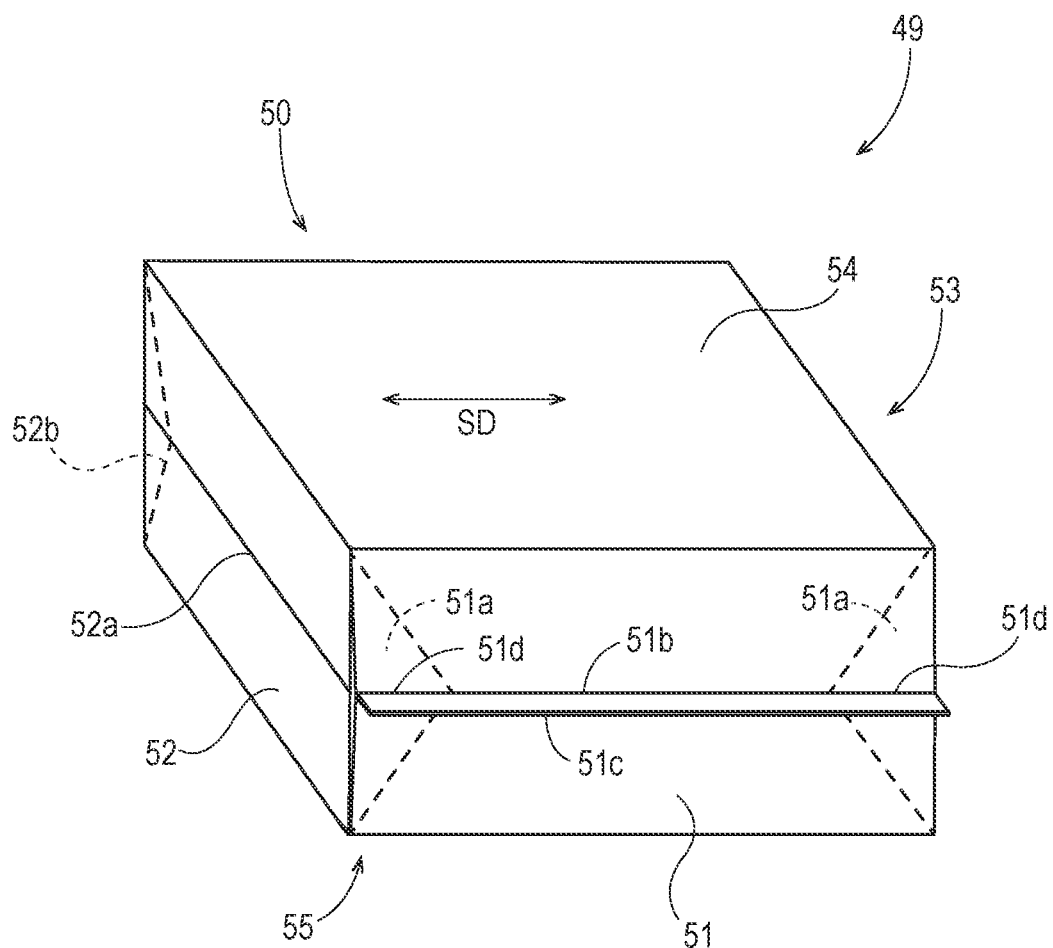
FIG. 5B is a perspective view of a film package that may be used to contain a stack of disposable absorbent articles such as the stack shown in FIG. 4.
Figure 5C:
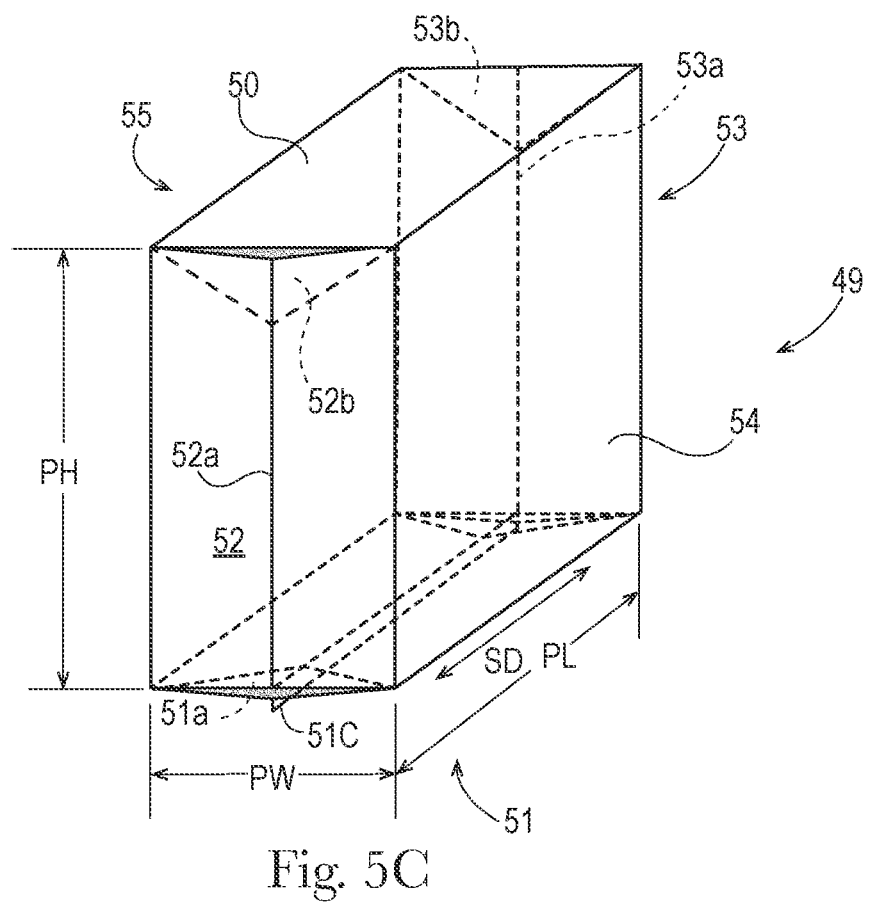
FIG. 5C is an alternative perspective view of the film package shown in FIG. 5B.

Referring to FIG. 5A, a bag structure 47 may be formed from a single sheet of film stock that is suitably folded to form bag gussets 52b, 53b and then joined along portions by bonding to form two side seams 52a, 53a on opposite side walls, to form bag structure 47 with no seam on a first package surface 50 (in the examples shown, the top surface), and open at the other end 48 (e.g., a gusseted bag structure). Thereafter, the bag structure may be filled by inserting product such as stack 40 of diapers through the open end 48. In a first example, stack 40 of diapers may be inserted first side 41 first, such that after insertion the fold noses inside the package are adjacent first package surface 50 (alternatively referred to as the bottom surface). In another example, stack 40 of diapers may be inserted first side 41 last (i.e., second side 42 first), such that after insertion the fold noses inside the package are adjacent second package surface 51. As may be appreciated from FIGS. 5B and 5C, the open end 48 opposite first package surface 50 may then be closed by suitably folding to form closing gussets 51a, bringing the film edges together, and bonding them together to form end seam 51b and second package surface 51. The bag structure 47 and stack 40 dimensions may be suitably selected and effected through design, folding, stacking, compression and packaging processes such the film of the package is taut about the stack at least along the stacking direction SD, to retain the individual diapers 10 in place within the stack 40, maintain stack compression, and maintain a neat, stable, approximate rectangular cuboid shape for the stack 40, and as a result, the package 49. Because the package 49 is formed of flexible polymer film, when suitably sized relative the stack 40 dimensions, package 49 will approximately assume the approximate rectangular cuboid shape and dimensions of the stack 40, when the package film is taut, or otherwise when any loose film is pressed against the stack. When the package film is taut about the stack along directions generally parallel with the stacking direction, in a manner that helps maintain stack compression along the stacking direction, the package will have a package length PL approximately corresponding to the stack length SL, and a package width approximately corresponding to the stack width SW. If the package structure is sized to provide no head space adjacent one or both of first and second sides 41, 42 of packaged stack 40 (i.e., no slack is present in the package film adjacent first and second sides 41, 42 of the stack after the package 49 is formed), the package will have a package height PH approximately corresponding to the stack height SH. In some examples, however, the film package structure may be sized to provide head space, and correspondingly, slack film, adjacent one or both of the first 41 and second 42 sides of stack 40, such as may be desired to provide a hood structure (described below) with extra height and overlapping capability.

To which reference is made above, the left and right side edges 34, 35 of the folded diapers in the stack 40, and corresponding third and fourth sides 43, 44 of stack 40 will be adjacent fifth and/or sixth package surfaces 54 and 55. It may be desired that the stack size and bag configuration and dimensions be selected such that fifth and sixth package surfaces 54 and 55 are the largest surfaces, or front and rear walls of the package. In this arrangement, when the film of the package is taut about the stack, the film of the third, fourth, fifth and sixth package surfaces 52, 53, 54 and 55 is in tension along directions approximately parallel to the approximate plane of the first surface 50, serving to at least partially maintain any compression of the stack 40 along the stacking direction SD. In some examples, the film stock may be supplied pre-printed with desired commercial artwork, graphics, trademark(s) and/or verbal or graphic product information, prior to formation of the bag structure.

The bonds forming any or all of the seams such as seams 52a, 53a and 51b may be created by welding. (Herein, "weld" refers to a union between separate portions of film stock, effected by application of direct or indirect (e.g., ultrasonic) heating energy and pressure that causes separate portions of the film to at least partially melt and fuse together to some extent, forming a bonded area, joint or seam which cannot be separated without substantial destruction to the remainder of one or both joined portions.) If bag-forming and/or packaging machinery forms welds in the film that join the film stock to itself by applying heating energy that causes the film to fuse to itself, it may be desirable that the film stock be multilayer film, and that the layer(s) to be brought into contact and fused be formed of polymer(s) that have lower melting temperature(s) than those of the polymer (s) used to form the other layer(s). This enables heating energy to be applied to a degree sufficient to heat the layer(s) in contact and cause them to fuse, but not sufficient to cause undesired melting and deformation of the other layer(s), which could cause the package to be misshapen and/or displace and/or distort printing on the film stock.

A multilayer film may be co-formed (such as by coextrusion), or in another example, individual layers may be separately formed and then laminated together following their formation, by use of a suitable laminating adhesive. In this latter example, an advantage provided is that one of the layers may be printed on one side before lamination. Following that, the printed side may be faced inward (facing the other layer(s)) during lamination, such that it is protected by the other layer(s) from abrasion and wear in the finished film product, thereby preserving the integrity of the printed images, graphics, verbal content, etc. A suitable multilayer film may be formed of one or more polyolefins, such as polypropylene and polyethylene. In one example, the stock film may have at least two layers, including a first layer of predominately polyethylene and second layer of predominately polypropylene. In one example, a layer formed of predominately polypropylene having a first relatively higher melting temperature, and a layer of predominately polyethylene having a second relatively lower melting temperature, may be used to form the outer and inner layers, respectively. In another example, an inner layer may be formed predominately of a first type of polyethylene having a relatively lower melting temperature, and an outer layer may be formed predominately of a second type of polyethylene having a relatively higher melting temperature.

In an application such as described herein, a multilayer film may be preferred. A multilayer film may have layers of polymer compositions particularly chosen for the characteristics they impart to the film. For example, one or two outer skin layers may be formed of compositions chosen for, e.g., surface gloss; printability; smooth feel; pliability; low noise generation (upon being handled and manipulated, as by a consumer); relatively lower melt temperature and fusibility/weldability; or any combination of these characteristics. One or more intermediate layers may be formed of compositions chosen for, e.g., tensile strength; stiffness; toughness; suitability for inclusion of blended-in recycled material; environmentally-friendly and/or sustainable material sourceability; relatively higher melt temperature; co-extrusion compatibility with adjacent layers (such that strong bonding between layers occurs upon co-extrusion); or any combination of these characteristics. For film stock in which only one side of the film will be placed in contact with itself and welded, a two-layer film may suffice. For film stock in which both sides of the film will be placed in contact with itself and welded, a film having at least three layers, with two outside skin layers that are weldable, may be desired. It will be appreciated that a package having the configuration depicted in FIGS. 5B and 5C requires the film to be welded to itself on both sides—on the generally outer film surface at the gussets 51a, 52b and 53b, and on the generally inner film surface along all other portions of the seams 51b, 52a and 53a.

Film Composition

A multilayer film may include first outside skin layer, second outside skin layer, and intermediate layer disposed between the skin layers. Each of the layers may include a base polymer. Base polymers may include polyolefins, particularly polyethylenes, polypropylenes, polybutadienes, polypropylene-ethylene interpolymer and copolymers having at least one olefinic constituent, and any mixtures thereof. Certain polyolefins can include linear low density polyethylene (LLDPE), low density polyethylene (LDPE), medium density polyethylene (MDPE), high density polyethylene (HDPE), isotactic polypropylene, random polypropylene copolymers, impact modified polypropylene copolymer, and other polyolefins which are described in PCT Application Nos. WO 99/20664, WO 2006/047374, and WO 2008/086539. Other base polymers such as polyesters, nylons, polyhydroxyalkanoates (or PHAs), copolymers thereof, and combinations of any of the foregoing may also be suitable. In addition, polyolefin plastomers and elastomers could be used to form the multi-layer polymeric films. Examples of such suitable polyolefin plastomers and elastomers are described in U.S. Pat. No. 6,258,308; U.S. Publication No. 2010/0159167 A1; and PCT Application Nos. WO 2006/047374 and WO 2006/017518. In one embodiment, such polyolefin plastomers and/or elastomers may comprise up to 25% by volume of the multi-layer polymeric film. Other useful polymers include poly-α-olefins such as those described in PCT Application No. WO 99/20664 and the references described therein.

In some examples, one or both of the skin layers may be formed of predominately MDPE, LDPE or LLDPE, more preferably LLDPE. A skin layer formed of predominately LLDPE may be particularly preferred because it imparts the skin layer with a good combination of weldability, relatively low melt temperature, printability (compatibility with currently commercially available printing inks), smooth surface finish, low noise, and a soft and pliable feel. In some examples, an intermediate layer may be formed of predominately HPDE, MDPE or LDPE, more preferably MDPE. An intermediate layer formed of predominately MDPE may be particularly preferred with one or more skin layers formed predominately of LLDPE because it imparts the intermediate layer with a good combination of relatively higher melt temperature, co-extrusion compatibility with the skin layer (s), pliability, toughness and tensile strength.

In alternative examples, an intermediate layer may be formed partially or predominately of a thermoplastic polymer other than polyethylene, such as any of the polymers identified above, or any polymers identified as suitable for intermediate layers in, for example, U.S. Pats. Nos. 9,169, 366 and 5,261,899; and U.S. Pat. Apps. Pub. Nos. 2015/03433748; 2015/0104627; and 2012/0237746, including bio-polymers or polymers having bio-based content as described in the latter three publications, such as, but not limited to, polylactic acid and thermoplastic starch. Additionally, an intermediate layer may include recycled thermoplastic polymer of any of the above-described types.

For purposes of balancing economy of polymer usage and maximization of tensile strength of the film, it may be desired that the total caliper of the film fall within a range of from 40 μm to 100 μm, more preferably from 50 μm to 90 μm, and even more preferably from 60 μm to 80 μm. For purposes of balancing economy of polymer usage, tensile strength and weldability, it may be desired that a three-layer film as described herein have a first and second skin layers each constituting from 15 percent to 35 percent of the weight of the film, and an intermediate layer constituting from 30 percent to 70 percent of the weight of the film.

Tie Layers

A multi-layer film as contemplated herein may comprise one or more tie layers disposed between other layers. A tie layer may be necessary when the polymers of adjoining layers would not otherwise be miscible or compatible so as to bond to each other during extrusion. For example, a tie layer between a polyethylene skin layer and an intermediate layer having a large polylactic acid content may be deemed desirable. Thus, for example, in a multilayer film having three main layers—two skin layers and an intermediate layer disposed between them, tie layers may be disposed between the intermediate layer and each of the skin layers. A tie layer may include one or more functionalized polyolefins. In some example, a tie layer may include from 5%, 10%, 20%, 30%, 40% or 45% to 55%, 60%, 70%, 80%, 90%, or 100%, by weight of the tie layer, of the one or more functionalized polyolefins. A tie layer may consist essentially of the one or more functionalized polyolefins.

For example, because of the significant difference in polarity between polylactic acid (PLA) and polyolefins, blends of these components typically result in incompatible systems with poor physical properties. A multilayer film having predominately polyethylene skin layers sandwiching an intermediate layer including PLA may also include one or more tie layers between the skin layers and the intermediate layer. This particular multi-layer structure may provide the MD and/or CD tensile properties useful for products currently made from polyethylene while incorporating a renewable feedstock (PLA). This arrangement may also enable downgauging (i.e., caliper reduction or basis weight reduction) of the film resulting from improvements in stiffness that can be used to drive sustainability and/or used as a cost savings.

The tie layer may comprise a functionalized polyolefin that possesses a polar component provided by one or more functional groups that is compatible with the PLA of the intermediate layer(s) and a non-polar component provided by an olefin that is compatible with one or more polyolefins of the adjacent skin layer. The polar component may, for example, be provided by one or more functional groups and the non-polar component may be provided by an olefin. The olefin component may generally be formed from any linear or branched a-olefin monomer, oligomer, or polymer (including copolymers) derived from an olefin monomer. The a-olefin monomer typically has from 2 to 14 carbon atoms and preferably from 2 to 6 carbon atoms. Examples of suitable monomers include, but not limited to, ethylene, propylene, butene, pentene, hexene, 2-methyl-1-propene, 3-methyl-1-pentene, 4-methyl-1-pentene, and 5-methyl-1-hexene. Examples of polyolefins include both homopolymers and copolymers, i.e., polyethylene, ethylene copolymers such as EPDM, polypropylene, propylene copolymers, and polymethylpentene polymers.

An olefin copolymer can include a minor amount of non-olefinic monomers, such as styrene, vinyl acetate, diene, or acrylic and non-acrylic monomer. Functional groups may be incorporated into the polymer backbone using a variety of known techniques. For example, a monomer containing the functional group may be grafted onto a polyolefin backbone to form a graft copolymer. Such grafting techniques are well known in the art and described, for instance, in U.S. Pat. No. 5,179,164. In other embodiments, the monomer containing the functional groups may be copolymerized with an olefin monomer to form a block or random copolymer. Regardless of the manner in which it is incorporated, the functional group of the compatibilizer may be any group that provides a polar segment to the molecule, such as a carboxyl group, acid anhydride group, acid amide group, imide group, carboxylate group, epoxy group, amino group, isocyanate group, group having oxazoline ring, hydroxyl group, and so forth. Maleic anhydride modified polyolefins are particularly suitable for use in the present invention. Such modified polyolefins are typically formed by grafting maleic anhydride onto a polymeric backbone material. Such maleated polyolefins are available from E. I. du Pont de Nemours and Company under the designation Fusabond, such as the P Series (chemically modified polypropylene), E Series (chemically modified polyethylene), C Series (chemically modified ethylene vinyl acetate), A Series (chemically modified ethylene acrylate copolymers or terpolymers), or N Series (chemically modified ethylene-propylene, ethylene-propylene diene monomer ("EPDM") or ethylene-octene). Alternatively, maleated polyolefins are also available from Chemtura Corp. under the designation POLYBOND and Eastman Chemical Company under the designation Eastman G SERIES, and AMPLIFYTM GR Functional Polymers (maleic anhydride grafted polyolefins). Other examples include LOTADER AX8900 (polyethylene-methyl acrylate-glycidyl methacrylate terpolymer) and LOTADER TX8030 (polyethylene-acrylic ester-maleic anhydride terpolymer) available from Arkema, Columbes, France.

In some aspects, the tie layer can be a resin composition as disclosed in U.S. Pat. No. 8,114,522. This resin composition includes a modified PO resin and a terpene resin. Alternatively, it includes a polylactic acid resin, a modified polyolefin resin, and a hydrogenated petroleum resin. These compositions are suitable for use as a tie layer between the outer layer and the core layer.

In some examples, an outer layer and tie layer may be essentially combined as an outer layer by incorporating a functionalized polyolefin into one or both of the outer layers.

In these instances, the multi-layer film may comprise 3 or 4 layers. In the case of a 3 layer film, the film may comprise a first outer layer comprising a polyolefin and/or a functionalized polyolefin, one or more core layers, and a second outer layer comprising a polyolefin and/or a functionalized polyolefin). In the case of a 4 layer film, the film may comprise a first outer layer comprising a polyolefin and/or a functionalized polyolefin, one or more core layers, a tie layer, and a second outer layer comprising a polyolefin.

Additives

Any of the layers of the multi-layer film may comprise small amounts of one or more additives.

Typically, the additives may comprise less than about 10%, 5%, 4%, 3%, 2%, 1%, 0.5%, 0.1% or 0.01% by weight of the layer of the additive. Some non-limiting examples of classes of additives contemplated include perfumes, dyes, pigments, nanoparticles, antistatic agents, fillers, and combinations thereof. The layers disclosed herein can contain a single additive or a mixture of additives. For example, both a perfume and a colorant (e.g., pigment and/or dye) can be present.

A pigment or dye can be inorganic, organic, or a combination thereof. Specific examples of pigments and dyes contemplated include pigment Yellow (C. I. 14), pigment Red (C. I. 48:3), pigment Blue (C. I. 15:4), pigment Black (C. I. 7), and combinations thereof. Specific contemplated dyes include water soluble ink colorants like direct dyes, acid dyes, base dyes, and various solvent soluble dyes. Examples include, but are not limited to, FD&C Blue 1 (C. I. 42090:2), D&C Red 6(C. I. 15850), D&C Red 7(C. I. 15850:1), D&C Red 9(C. I. 15585:1), D&C Red 21(C. I. 45380:2), D&C Red 22(C. I. 45380:3), D&C Red 27 (C. I. 45410:1), D&C Red 28(C. I. 45410:2), D&C Red 30(C. I. 73360), D&C Red 33(C. I. 17200), D&C Red 34(C. I. 15880:1), and FD&C Yellow 5(C. I. 19140:1), FD&C Yellow 6(C. I. 15985:1), FD&C Yellow 10(C. I. 47005:1), D&C Orange 5(C. I. 45370:2), and combinations thereof.

Contemplated fillers include, but are not limited to, inorganic fillers such as, for example, the oxides of magnesium, aluminum, silicon, and titanium. These materials can be added as inexpensive fillers or processing aides. Other inorganic materials that can function as fillers include hydrous magnesium silicate, titanium dioxide, calcium carbonate, clay, chalk, boron nitride, limestone, diatomaceous earth, mica glass quartz, and ceramics. Additionally, inorganic salts, including alkali metal salts, alkaline earth metal salts, phosphate salts, can be used. Additionally, alkyd resins can also be added to the composition. Alkyd resins can comprise a polyol, a polyacid or anhydride, and/or a fatty acid.

Additional contemplated additives include nucleating and clarifying agents for the thermoplastic polymer. Specific examples, suitable for polypropylene, for example, are benzoic acid and derivatives (e.g., sodium benzoate and lithium benzoate), as well as kaolin, talc and zinc glycerolate. Dibenzlidene sorbitol (DBS) is an example of a clarifying agent that can be used. Other nucleating agents that can be used are organocarboxylic acid salts, sodium phosphate and metal salts (e.g., aluminum dibenzoate). In one aspect, the nucleating or clarifying agents can be added in the range from 20 parts per million (20 ppm) to 20,000 ppm, or from 200 ppm to 2000 ppm, or from 1000 ppm to 1500 ppm. The addition of the nucleating agent can be used to improve the tensile and impact properties of the finished composition.

Additional contemplated additives include slip agents for purposes of reducing the coefficient of friction on one or both of the two outside surfaces of the film, or as antiblocking agents. Suitable additives for this purpose may include but are not limited to fatty amides, for example, erucamide. Additives may also include antioxidants such as BHT, and IRGANOX products, for example, IRGANOX 1076 and IRGANOX 1010. IRGANOX products are available from BASF Corporation, Florham Park, N.J., USA. Antioxidants may help reduce degradation of the film through oxidation, particularly during processing.

Contemplated surfactants include anionic surfactants, amphoteric surfactants, or a combination of anionic and amphoteric surfactants, and combinations thereof, such as surfactants disclosed, for example, in U.S. Pat. Nos. 3,929,678 and 4,259,217, and in EP 414 549, WO93/08876, and WO93/08874.

Contemplated nanoparticles include metals, metal oxides, allotropes of carbon, clays, organically modified clays, sulfates, nitrides, hydroxides, oxy/hydroxides, particulate water-insoluble polymers, silicates, phosphates and carbonates. Examples include silicon dioxide, carbon black, graphite, grapheme, fullerenes, expanded graphite, carbon nanotubes, talc, calcium carbonate, bentonite, montmorillonite, kaolin, zinc glycerolate, silica, aluminosilicates, boron nitride, aluminum nitride, barium sulfate, calcium sulfate, antimony oxide, feldspar, mica, nickel, copper, iron, cobalt, steel, gold, silver, platinum, aluminum, wollastonite, aluminum oxide, zirconium oxide, titanium dioxide, cerium oxide, zinc oxide, magnesium oxide, tin oxide, iron oxides (Fe203, Fe304) and mixtures thereof. Nanoparticles can increase strength, thermal stability, and/or abrasion resistance of the compositions disclosed herein, and can give the compositions electric properties.

Contemplated anti-static agents include fabric softeners that are known to provide antistatic benefits. These can include those fabric softeners having a fatty acyl group that has an iodine value of greater than 20, such as N,N-di(tallowoyl-oxy-ethyl)-N,N-dimethyl ammonium methylsulfate.

In particular aspects, the filler can comprise renewable fillers. These can include, but are not limited to, lipids (e.g., hydrogenated soybean oil, hydrogenated castor oil), cellulosics (e.g., cotton, wood, hemp, paperboard), lignin, bamboo, straw, grass, kenaf, cellulosic fiber, chitin, chitosan, flax, keratin, algae fillers, natural rubber, nanocrystalline starch, nanocrystalline cellulose, collagen, whey, gluten, and combinations thereof.

Particular combinations of film layers, film layer compositions and pigment additives for maximizing package film opacity while providing a film that effectively balances weldability, tensile strength and cost effectiveness are described in PCT Application No. CN2016/088098, the disclosure of which is incorporated herein by reference.

Opening Features

Figure 6A:
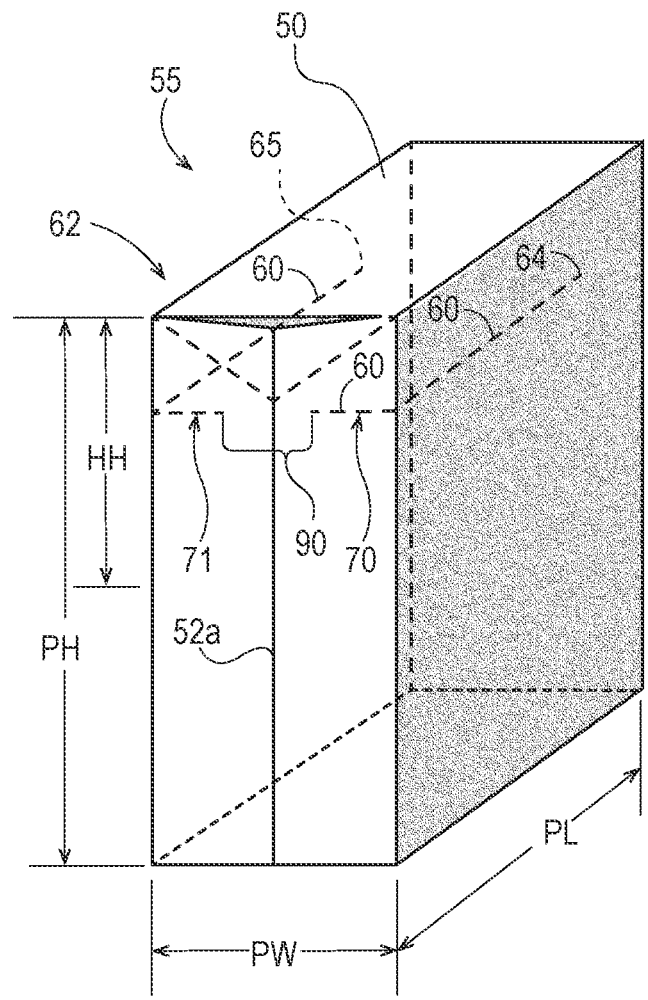
FIG. 6A is a perspective view of a film package that may be used to contain a stack of diapers such as the stack shown in FIG. 4, depicting a configuration of a path of perforations or scoring, in one example.
Figure 6B:
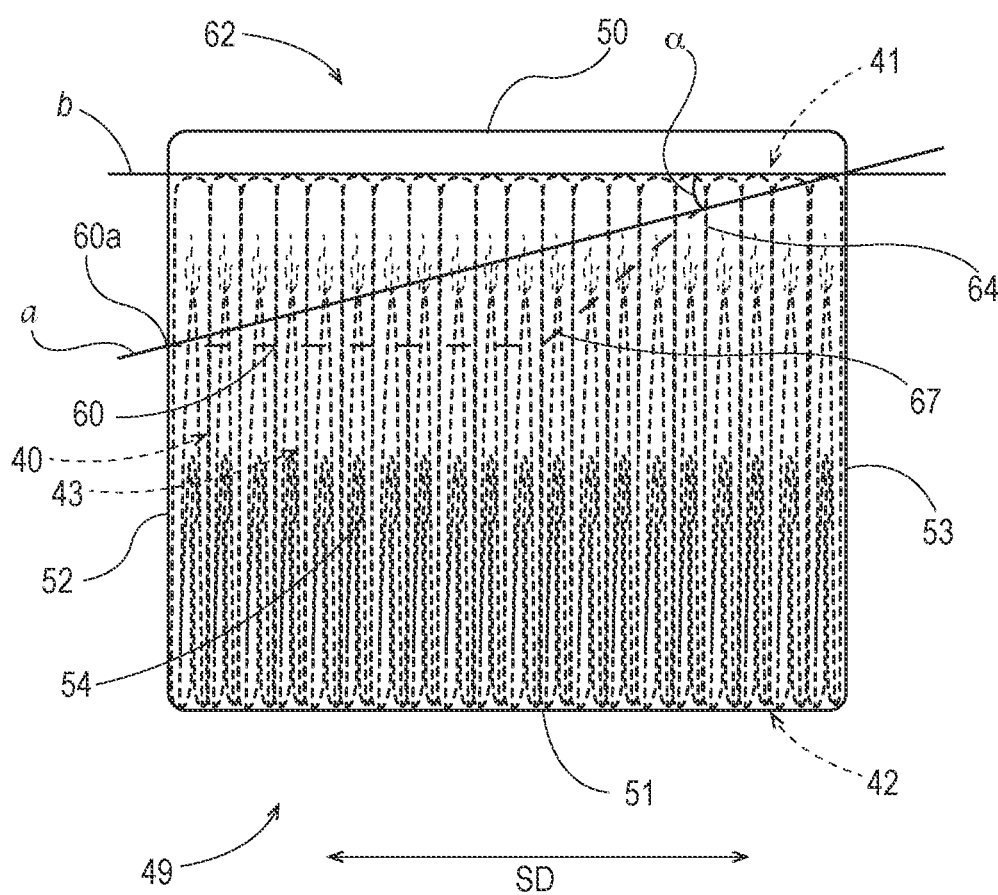
FIG. 6B is a side view of a film package that may be used to contain a stack of diapers such as the stack shown in FIG. 4, depicting a configuration of a path of perforations or scoring along the surface shown, in an alternative example.

Referring to FIGS. 6A and 6B, a film package containing a stack of disposable absorbent articles such as disposable diapers, training pants or adult incontinence pants, may be imparted with features that facilitate opening without unwanted deformation or destruction of the package, so that the opened packaged may be used, following opening, as a container to store the supply of unused product.

In the example depicted in FIG. 6A, the package may be provided with two or more perforation lines. A first perforation line 70 extends from the front wall towards the seam provided on one of the first and second side walls. A second perforation line 71 extends from the rear wall towards the same seam. A stress dispersion area 90 connects the first perforation line and the second perforation line over the seam. Collectively, the first perforation line, the second perforation line and the stress dispersion area define an opening path 60. The stress dispersion area has a length of at least 8 mm, 10 mm, 15 mm, 20 mm and 25 mm. The stress dispersion area is intended to be long enough to disperse any forces applied to the perforation line during, for example, transport of the packs prior to use. For example, the seam leads to a gusset formed at the top and bottom of at least one of the side walls. Buyers often grab the bag in the area of the gusset upon purchase thus introducing stress along the short wall. In such circumstances, without the stress dispersion area, the bag may prematurely open. This is also the case for other handles that are in line with the seam. The length of the stress dispersion area addresses the need for balance between avoiding unintentional and premature opening of the package, while still enabling easy and neat opening.

Preferably, the stress dispersion area 90 is less than 80%, less than 75%, less than 70%, less than 65%, less than 60% or less than 50% of the total width of the side wall. Typically, the width of the side wall is equivalent to the width of a folded pad or diaper and is typically around 80 mm to 100 mm wide. Thus, preferably, the stress dispersion area is less than 65 mm, 60 mm, 50 mm, 45 mm or 40 mm. In this respect, there is a tradeoff between ensuring the stress dispersion area is long enough that premature opening of the package is prevented, but not so long that the package does not open along a continuous path. Furthermore, it is preferable that the stress dispersion free line is not perceptible to a user. The stress dispersion area may be evenly split over the seam, or it may be longer or bigger on one side of the seam relative to the other side of the seam.

Figure 11:
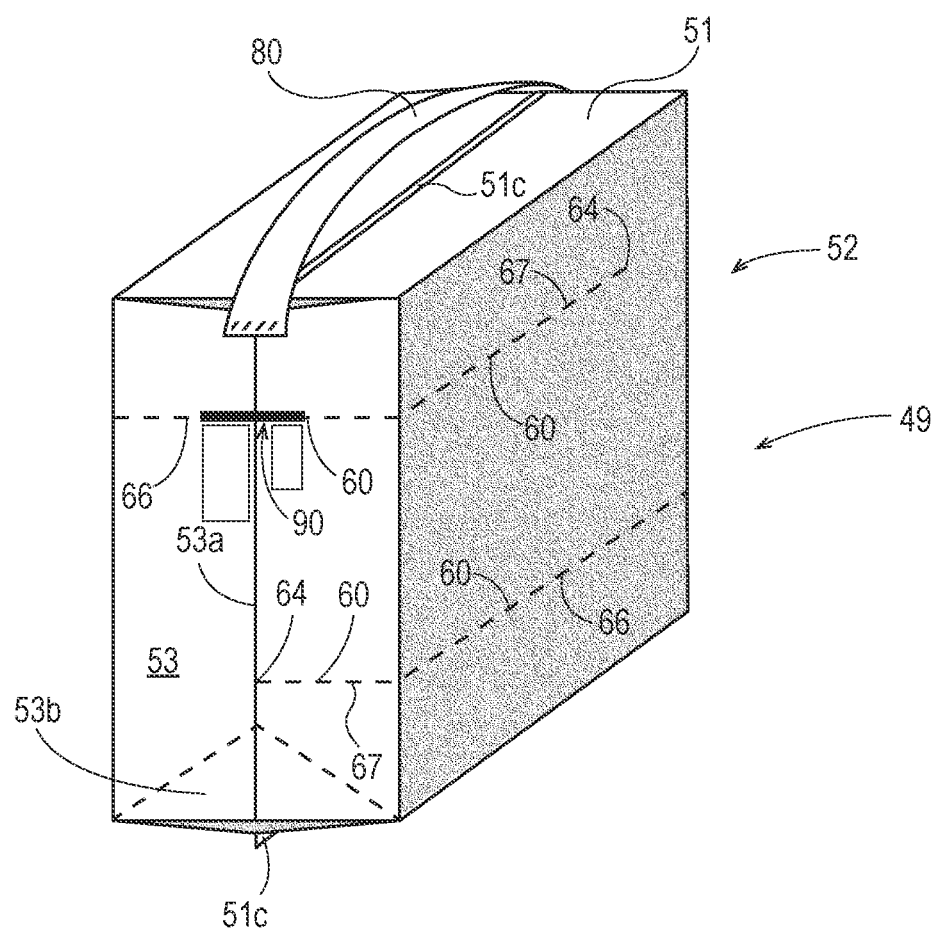
FIG. 11 is a perspective view of a film package that may be used to contain a stack of diapers such as the stack shown in FIG. 4, depicting several possible configurations of paths of perforations or scoring, and having another example of a carrying handle disposed at a second location.

In FIGS. 6A and 11, the stress dispersion area 90 is shown as an area between the first and second perforation lines that is absent of any perforations, scoring or markings. The absence of any perforations in this area immediately over the seam, and thus falling in line with an area in which the package my potentially be grabbed by a user, dissipates any forces encountered in the package via such grabbing. This dissipation prevents premature opening of the pack, without limiting the potential to easily open the pack when desired.

Figure 7:
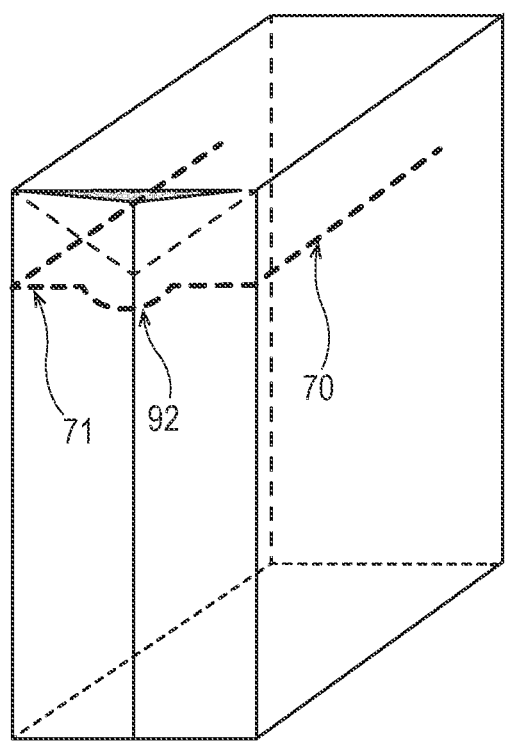
FIG. 7 is a perspective view of a film package that may be used to contain a stack of diapers such as the stack shown in FIG. 4, depicting an alternative example of a stress dispersion area.
Figure 8:
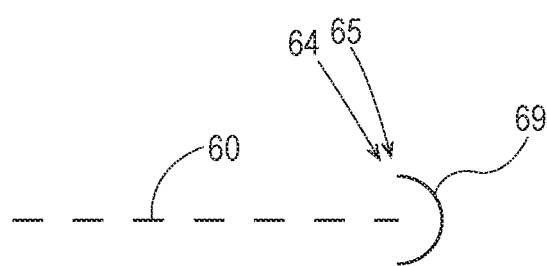
FIG. 8 is a depiction of an endpoint of a path of perforations or scoring, including a tearing stress dispersion feature.
Figure 9:
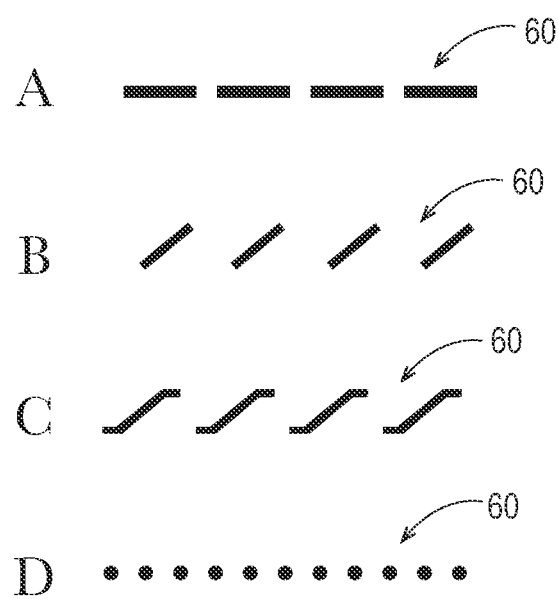
FIG. 9 is a perspective view of a film package that may be used to contain a stack of diapers such as the stack shown in FIG. 4, depicting several possible configurations of paths of perforations or scoring, and having an example of a carrying handle disposed at a first location.

In FIG. 7, the stress dispersion area 92 is shown as an area of perforations following a different trajectory to the first and second perforation lines. In this example, the line of perforations are continued, however, in the stress dispersion area, the perforations are located further away from a top surface of the package than the first and second perforation lines. This increases the distance to the breakline at the area where stress is likely to be experienced in the package when it is grabbed by a user. Thus, any increase in the distance of perforations over the seam can facilitate some stress dispersion. In the embodiment shown, the line of perforations is continued through the stress dispersion area such that the package continues to be easy to open. Furthermore, such a stress dispersion area that extends slightly further in the area over the seam may provide a convenient lip 92 to the hood that serves as an indicator to consumers of where to open the pack.

Figure 12:
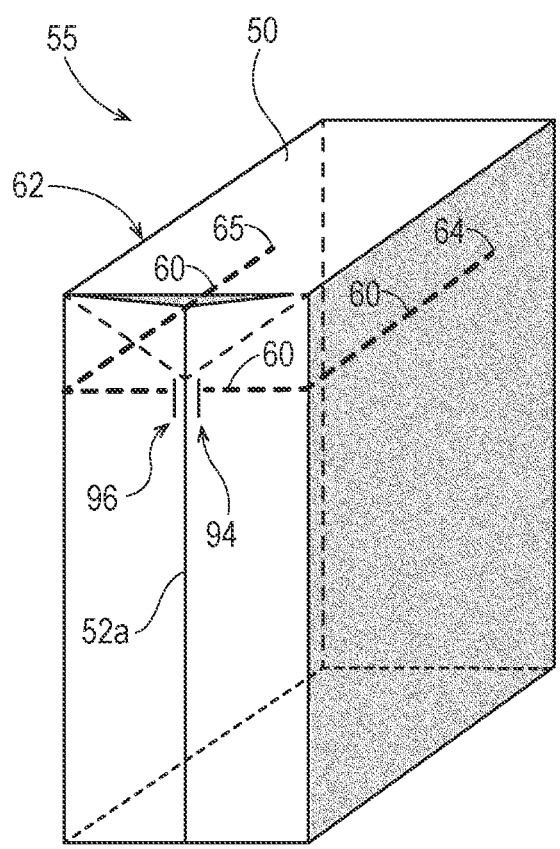
FIG. 12 is a perspective view of a film package that may be used to contain a stack of diapers such as the stack shown in FIG. 4, depicting additional possible configurations of paths of perforations or scoring.

FIG. 12 shows a further embodiment where first 94 and second 96 vertical perforations are provided between the respective ends of the first and second perforation lines and the seam. Although these are shown as vertical perforations (i.e., parallel to a longitudinal axis of the package), it will be appreciated that they could have any angle between 0° and 45° relative to the longitudinal axis and still be effective at dissipating stress in this region.

In addition to the examples shown, it will be appreciated that there are multiple forms the stress dispersion area may take, for example, vertical or angled perforations, scoring that does not extend the whole way through the package, raised or depressed textures, indentations, embossing or creases. The preceding examples either deflect stress away from the first and second perforation lines or they provide an area that requires greater force to open (relative to the first and second perforation lines). In one example, the stress dispersion area may comprise a single, uninterrupted line of laser scoring that does not entirely penetrate the film but is configured to promote neat tear propagation along the path, such as described in U.S. Application Pub. No. 2015/0266663, the disclosure of which is incorporated herein by reference. Thus, any of the preceding configuration of stress dispersion areas may be used to prevent or minimize the possibility of premature opening.

The perforation lines may be continuous. (For purposes herein, a "continuous" path of perforations or scoring is a singular path of individual, successive, mechanically-created partial or complete perforations, a singular path of individual, successive laser-scored partial or complete perforations, or a continuous, singular path of laser scoring, that is uninterrupted by an unperforated/unscored portion of the film of a length between successive perforations or scoring greater than 8 mm.)

Figure 10:
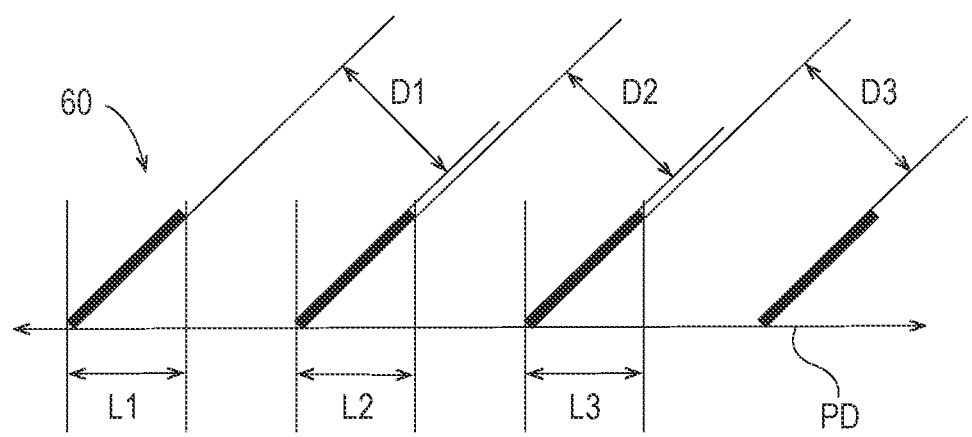
FIG. 10 is a perspective view of a film package that may be used to contain a stack of diapers such as the stack shown in FIG. 4, depicting several possible configurations of paths of perforations or scoring, and having another example of a carrying handle disposed at a first location.

Individual perforations defining a path 60 may have any configuration suitable for propagating a tear in the package film along the path. Non-limiting examples are depicted in FIGS. 9A-9D. Where the path 60 of perforations comprises a plurality of individual mechanically-created perforations or individual laser-scored perforations, it may be desired that the path have a cut-to-land ratio of at least 0.67:1 and no greater than 3:1. For film packages of the type contemplated herein, it is believed that a cut-to-land ratio within this range strikes a suitable balance between providing for ease of package opening and minimized strain deformation of the film along the path during opening, and avoiding premature, unintended package bursting or opening, and retaining structural integrity of the package during shipping, handling and other events prior to retail purchase and intentional opening by the consumer. (For purposes herein, the "cut-to-land ratio" of a path of perforations is the ratio of the aggregate of the lengths of the perforations extending along the path direction, to the aggregate of the minimum distances of unperforated/unscored portions of the film between successive perforations. Referring to FIG. 10, for example, in which a portion of a path of successive diagonally-tilted rectangular perforations is depicted lying along path direction PD, the cut-to-land ratio is (L1+L2+L3):(D1+D2+D3).

For both ease of opening and simplification of manufacturing, it may be preferred that the path 60 of perforations or scoring defining the hood structure 62 does not traverse a gusset (such as gussets 52b and 53b), because a gusset structure includes more than one layer of package film (e.g., three layers), making propagation of a neat tear along the path more difficult.

When the first side 41 of stack 40 is adjacent either the first package surface 50 or the second package surface 51, it may be desired that any portions of the first and second perforation lines that traverse any of third, fourth, fifth or sixth package surfaces 52, 53, 54 and 55 be oriented at an angle that is 45 degrees or less, more preferably 30 degrees or less, even more preferably 15 degrees or less, and most preferably substantially parallel, with the approximate plane of the first side 41 of stack 40. This is because, as noted above, the film of package surfaces 52, 53, 54 and 55 will be in tension along directions substantially parallel with this plane, as the package contains the stack and maintains stack compression along the stacking direction SD. A path 60 of perforations or scoring on any of surfaces 52, 53, 54 and 55 that is substantially transverse to a direction of elevated film tension increases the risk of unintended, premature opening (rupture) of the package at a location along the path 60, prior to the time a consumer intends to open the package to access the contents. Accordingly, in the examples shown in FIG. 6A, all portions of path 60, which are present on one of package surfaces 52, 53, 54 and/or 55, are oriented substantially parallel with the approximate plane of surface 50. In some examples, the manufacturer may choose to create a non-linear or non-uniformly linear path 60 of perforations or scoring in the package film. In one example depicted in FIG. 6B, path 60 has a portion 67 extending from corner point 60a where it traverses a package corner, to an endpoint 64. Portion 67 follows a non-linear path across fifth package surface 54. To observe the principles reflected in the preceding paragraph, a first straight line a is established, connecting corner point 60a and endpoint 64 of path 60. A second straight line b is established, parallel each of the planes along first 41 and third 43 sides of stack 40 within the package, and intersecting line a. Angle a at the intersection of lines a and b may then be measured, and is a reflection of the extent to which path 60 traverses the stacking direction SD. This method of measuring and determining the desired limitations on an angle of a path 60 of perforations or scoring across a package surface will apply to any path configuration, for purposes herein. For the reasons explained in the preceding paragraph, it may be desired that angle a be 45 degrees or less, more preferably 30 degrees or less, even more preferably 15 degrees or less, and most preferably approximately zero. Additionally, while an angle α greater than zero such as depicted in FIG. 6B may provide a hood structure 62 that is relatively easier to flip open following initial package opening (resulting from relatively less distance between endpoint 64 to an adjacent package surface, e.g., package surface 50), the free edge portions of hood structure 62 below line a will have less support within the hood structure following opening, making them less secure (i.e., floppy), which may in some circumstances be deemed counter to purposes of providing satisfactory reclosure.

As noted, it may be desired that the package have a recloseability feature. It has been discovered through experimentation and observation of consumer behavior that an opening hood structure 62 having three sides each formed of a portion of one of the third, fourth, fifth or sixth package surfaces 52, 53, 54, 55, and a top formed of a portion of one of the first or second package surfaces 50, 51, as suggested in FIG. 6A, can provide an effective, easy to use cover over the supply of unused product, which can help guard against entry of airborne contaminants into the package. It has been discovered, surprisingly, that these configurations inherently promote consumer recognition and use of them as reclosing devices. In the example depicted in FIG. 6A, a hood structure 62 has three sides formed of portions of package surfaces 52, 54 and 55, and the top is formed by a portion of first package surface 50. The hood structure is formed when the consumer tears the package film completely along path 60 of perforations or scoring. After opening, the hood structure 62 may be reclosed by returning it to a position similar to the one it occupied with respect to the remainder of the package, prior to opening.

Through experimentation and observation of consumer behavior, it believed that the hood structure 62 preferably provides quick access and retrieval, using one's fingers, following package opening, for a majority of the individual articles in the stack 40, without requiring a reach far down inside the package. From observation it is believed that the proximity of the fold noses to the opening is preferred by consumers because it reduces effort by facilitating the quick tactile identification and grasping of an individual product for withdrawal from the stack and from the package. Thus, in the example depicted in FIG. 6A (herein designated a "long-short-long" or "LSL" path 60), the portions 67, 68 of path 60 defining the hood may have a stack direction path length PLSD of at least 60 percent, more preferably at least 65 percent, even more preferably at least 70 percent, of the package length (PL). At the same time, it may be desired that the hood structure not lift entirely away from the top of the stack, because this may reduce consumer recognition and use of the hood structure as a reclosing/covering device. Accordingly, in the example depicted in FIG. 6A, the portions 67, 68 of path 60 defining the hood may have a stack direction path length PLSD limited at 95 percent, more preferably 90 percent, and even more preferably 85 percent, of the package length (PL).

Through the above-referenced experimentation and observations, it is believed that consumers prefer the hood structure to have at least a minimum amount of material to grasp and pull back over the unused supply of articles in the package in the manner of a hood. Thus, in order for the LSL hood structure 62 such as depicted in FIG. 6A to have an appearance and function as such, it may be desired that the structure have a hood height HH of at least 40 mm, more preferably at least 45 mm and even more preferably at least 50 mm. For purposes herein, the hood height HH is measured with the stack 40 within the package urged all the way within the package (without adding any substantial compression of the stack height), against the first or second package surface 50 or 51 opposite the hood structure. With the stack urged to this position, and the package standing with its height vertical, the hood height HH is the largest measurable distance between the path 60 of perforations or scoring where it traverses a package corner, and the nearest of the first or second sides 41, 42 of the stack (which during measurement with the package standing as described, will be proximate the apparent "top" relative the top-opening hood structure).

In some examples (not shown) it may be preferred that the package include some head space therewithin, and within the hood structure. This results in some slack film material in the hood structure prior to package opening. This extra material provided along the direction of the package height gives the consumer extra material to conveniently grasp when reclosing the package with the hood structure. Additionally, the extra film material along the direction of the package height enables the consumer to pull the hood structure down over the stack and down over and beyond the path perforations or scoring on the lower portion of the package, easily and conveniently overlapping some of the film material of the hood structure over the film material below the path 60, providing for more complete reclosure and more complete coverage of the unused supply of product within the package.

Referring to FIG. 10, in order to reduce chances that a consumer opening the package will tear the package film past endpoints 64, 65 of the path 60 of perforations or scoring, and deform the package film and/or reduce the utility of the hood structure 62, it may be desired to include a tactilely perceivable tearing stress dispersion feature 69 proximate one or both endpoints 64, 65. In the example depicted in FIG. 10, tearing stress dispersion feature 69 is a semi-circular perforation or cut running transverse to the direction of the path 60, which serves to disperse tearing stresses concentrated at the endpoint, and obstruct tear propagation in a way that may be perceived tactilely by the consumer they are opening the package. It will be appreciated that tearing stress dispersion feature 69 may have other forms including other shapes of cuts or perforations through the film that extend transversely to the direction of the path 60, added reinforcing strips, tapes, etc.

Stress dispersion features can also be placed at varying points along a path of perforations or scoring besides the end points. This approach can permit relatively small openings and hood structures. For example, some consumers (e.g., hygiene-sensitive consumers who seek to open the packaging minimally for protection, or those who invest in minimal effort to open and close the package) utilize a corner lift that is enabled by a LSL path or combination LSL and SLS path. While these paths can enable a corner lift, employment of stress dispersion features can maintain the desired size of the opening and corresponding hood structure.

Through experimentation and observation of consumer behavior it is believed that consumers prefer to have most immediate access to a side of the stack 40 at which the single fold noses 30 of the diapers are present, i.e., first side 41. This may be because consumers find it easiest to quickly identify, grasp and withdraw a single product item from the stack by the tactile feel of the single fold noses. Conversely, the plurality of side and waist edges of a single folded diaper in a stack are typically less distinguishable by touch, from those of neighboring diapers in the stack. This preference may indicate a further preference that all fold noses of the stack be present at only one side the stack, i.e., only one of sides 41, 42. For easiest consumer access to the fold noses, it may be desired that the path 60 of perforations or scoring and the portions 66, 67 and 68 thereof, be disposed generally closer to one of the package surfaces, e.g., one of surfaces 50, 51, that is adjacent the single fold noses of the diapers in the stack 40, thereby locating hood structure 62 proximate first side 41 of stack 40—and preferably the surface most proximate the fold noses.

When it is defined by fold noses 30, the first side 41 of a stack 40 is often more flat and firm, than the opposing second side 42. For marketing purposes it may be preferred to design the package with the expectation that one of the larger surfaces 54, 55 will face outward (i.e., face the aisle) when the package is on the shelf in a retail store. This provides for consumer view of one of the larger surfaces, with more surface area available that can be imprinted with commercial artwork, graphics and product information. Thus, the package and stack may be configured such that the first side 41 of the stack 40 with the fold noses is located at, and forms the shape of, the "bottom" of the package as it is shelved, and the sides of the stack with the side edges 34, 35 of the diapers will be respective adjacent the larger surfaces 54, 55, which will be substantially vertical when the package rests on its "bottom." The firmer, flatter first side 41 of the stack 40 provides for a firmer, flatter package "bottom," that enhances the ability of the package to rest stably on the shelf, and be less prone to leaning and/or tipping over. Thus, it may be desired to locate the path 60 of perforations or scoring, defining a hood structure 62, nearer the "bottom" of the package, so as to define a hood structure proximate the first side of the stack. Visible verbal and graphic information on sides 54 and 55 may be arranged so as to appear upright and legible with the package resting with the first side of the stack at the bottom.

It may be desired to provide one or more indicia on the package that visibly, tactilely and/or verbally identify the location of the path 60 of perforations or scoring. The one or more indicia may include, but are not limited to, an imprinted path marking or tracing path 60, of a color that visibly contrasts with surrounding package printing; tactilely perceivable indicia; verbal indicia; other graphic indicia or any combination thereof. In one example, the indicia may include embossing or other surface texturing of the film, configured to provide raised, tactilely perceivable features that suggest the presence of the path 60 of perforations or scoring for opening. In a particular example, embossing may be configured to suggest one or more ridges following lines or paths proximate and parallel to path 60. In another particular example, embossing may be configured to suggest one or more lines or paths of stitches following paths proximate and parallel to path 60. Additionally, the package may include verbal or graphic indicia that instruct or encourage the consumer to flip the package over, putting the perceived "top" side down and "bottom" side up, for opening and/or storage. Additionally, or alternatively, commercial artwork, graphics, and verbal information printed onto the film of the package may be configured in some examples to have an upright appearance regardless of which surface 50, 51 of the package is disposed at the top as the package is placed on a horizontal surface. In some examples, the printed material may be configured to suggest that either of surfaces 50, 51 can appropriately be deemed the "top" of the package.

The characteristic of the tactilely perceivable indicia and/or graphic indicia can vary significantly. The indicia can extend to a length that is less than, substantially the same as, or greater than a length of the path of perforations or scoring. In one example, a combination of tactilely perceivable indicia and graphic indicia are employed, wherein lengths of these two types of indicia are different. That is, graphic indicia may be included at a first length that does not disrupt the overall visual impression of the package artwork, and tactilely perceivable indicia is included at a second length that is greater than the first length. Alternative to or in addition to their respective extension lengths, positioning of the two types of indicia can vary on one or more of the package surfaces. For example, graphic indicia can primarily exist on a side surface (e.g., one of the third or fourth package surfaces) and optionally partially on an adjacent side surface (e.g., one of the fifth and sixth package surfaces and a package corner), while tactilely perceivable indicia primarily exist on a main package surface (e.g., one of the fifth and sixth package surfaces). In this scenario, a consumer's eyes are drawn to the graphic indicia to indicate where the path of perforations or scoring is located to help them to start the package opening process and then the consumer can utilize the tactilely perceivable indicia to guide their continued opening process to the fullest extent desired. By strategically locating the graphic indicia, artwork associated with a major package surface for marketing and educational purposes is not unduly disrupted by the graphic indicia. Thus, in one example, the package can comprise a first graphic comprising branding and marketing elements and a second graphic to highlight the path of perforations or scoring wherein the second graphic does not intersect the branding and marketing elements.

Other characteristics of the indicia can vary. For example, the graphic indicia can have varying color, hue, and/or dimensions. And the tactilely perceivable indicia can have varying dimensions (e.g., emboss depth), intensity, frequency or the like. Such characteristics can vary as step changes or gradually like in a gradient pattern.

Referring to FIG. 11, particularly for a larger package 49, it may be desired that the package include a carrying handle 80. In one example, a carrying handle 80 may be formed of a strip of polymer film. In a more particular example, the strip may have its long dimension oriented along the stack direction SD. The strip may be bonded by any suitable mechanism to portions of the package or package film. In another example depicted in FIG. 12, a carrying handle 80 may be formed of an extension of a fin 51c extending from the package from an end seam 51. The end seam fin 51c may have a handle cutout 81 made therethrough, providing a carrying handle 80.

Also as suggested in FIGS. 11, various configurations and locations for a path 60 of perforations or scoring are contemplated, and may be included in plurality and in any combination. As noted above, however, it may be desired that the package include at least a path 60 configuration and location that defines a hood structure proximate a side 41 or 42 of the stack 40 within the package, defined by fold noses. Thus, if the first side 41 of the stack is defined by fold noses and faces down in the examples depicted in FIGS. 11 and 12, it may be desired that a path 60 configuration defines a hood structure proximate the bottom of the package.

The dimensions and values disclosed herein are not to be understood as being strictly limited to the exact numerical values recited. Instead, unless otherwise specified, each such dimension is intended to mean both the recited value and a functionally equivalent range surrounding that value.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

We claim:

1. A package formed of flexible polymeric film, enclosing and wrapping a stack of folded disposable absorbent articles having an approximate rectangular cuboid shape, the package comprising:
   a) front, rear, first and second side walls and a top and bottom surface, defining an approximate rectangular cuboid shape;
   b) at least one seam extending from the top to the bottom surfaces of one of the side walls;
   c) a first perforation line extending from the seam partway along the front wall;
   d) a second perforation line extending from the seam partway along the rear wall;
   e) a stress dispersion area between the first perforation line and the second perforation line, wherein the stress dispersion area extends over the seam and is at least 8 mm long;
   wherein the flexible polymeric film comprises a blended-in recycled material.

2. The package of claim 1, wherein the flexible polymeric film comprises multiple layers with one layer comprising a thermoplastic polymer layer.

3. The package of claim 1, wherein the stress dispersion area extends over less than 80% of the total width of the side wall containing the seam.

4. The package of claim 1, wherein the stress dispersion area is less than 65 mm long.

5. The package of claim 1, wherein the stress dispersion area is an area comprising no perforations.

6. The package of claim 1, wherein the stress dispersion area comprises one or more perforations extending at an angle relative to the perforations forming the first and second perforation lines.

7. The package of claim 6, wherein the first and second perforation lines and the stress dispersion area extend substantially orthogonal to a longitudinal axis of the package.

8. The package of claim 6, wherein the stress dispersion area further comprises one or more perforations oriented parallel to a longitudinal axis of the package.

9. The package of claim 6, wherein the stress dispersion area comprises perforations located further away from the top surface than the first and second perforation lines.

10. A package formed of flexible polymeric film, enclosing and wrapping a stack of folded disposable absorbent articles having an approximate rectangular cuboid shape, the package comprising:
   a) front, rear, first and second side walls and a top and bottom surface, defining an approximate rectangular cuboid shape;
   b) at least one seam extending from the top to the bottom surfaces of one of the side walls;
   c) a first perforation line extending from the seam partway along the front wall;
   d) a second perforation line extending from the seam partway along the rear wall;
   e) a stress dispersion area between the first perforation line and the second perforation line, wherein the stress dispersion area extends over the seam and is at least 8 mm long;
   wherein the flexible polymeric film comprises from about 30% to about 70% blended-in recycled material.

11. The package of claim 10, wherein the flexible polymeric film comprises multiple layers with one layer comprising a thermoplastic polymer layer.

12. The package of claim 10, wherein at least 20% of the stress dispersion area is located on one side of the seam.

13. The package of claim 10, wherein 50% of the stress dispersion area is located on either side of the seam.

14. The package of claim 10, wherein the first and second perforations and the stress dispersion area are located from 20 mm to 70 mm from a top surface of the package.

15. The package of claim 10, further comprising a holding mechanism, wherein at least part of the holding mechanism is located at a top of the seam.

16. The package of claim 15, wherein the holding mechanism comprises one or more of: a handle having a first end attached to a top of the seam, a gusset located at the top of the seam, and an eyelet located at a top of the seam.

17. The package of claim 10, wherein the first and second perforation lines and the stress dispersion area are substantially parallel to the top of the package.

18. The package of claim 10, wherein the distance from the top surface varies along one or both of the first and second perforation lines.

19. The package of claim 10, wherein the cut to land ratio of the first and second paths of perforations is at least 0.67:1 and no greater than 3:1.

20. The package of claim 10, wherein the stress dispersion area is less than 65 mm long.

* * * * *